(12) United States Patent
Scheying et al.

(10) Patent No.: US 7,479,636 B2
(45) Date of Patent: Jan. 20, 2009

(54) DEVICE AND METHOD FOR ANALYZING A MATERIALS LIBRARY

(75) Inventors: Gerd Scheying, Stuttgart (DE); Steffen Katzenberger, Bad Liebenzell (DE); Thomas Brinz, Bissingen (DE); Joerg Jockel, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 518 days.

(21) Appl. No.: 10/863,068

(22) Filed: Jun. 7, 2004

(65) Prior Publication Data

US 2004/0256562 A1 Dec. 23, 2004

(30) Foreign Application Priority Data

Jun. 6, 2003 (DE) ................. 103 25 735

(51) Int. Cl.
*G01J 5/02* (2006.01)
(52) U.S. Cl. .................. 250/339.06; 250/349
(58) Field of Classification Search ........... 250/339.06, 250/339.07, 343, 341.8, 349, 341.7; 356/369; 359/355, 356
See application file for complete search history.

(56) References Cited

U.S. PATENT DOCUMENTS

| | | | |
|---|---|---|---|
| 4,477,190 A | | 10/1984 | Liston et al. |
| 5,959,297 A * | | 9/1999 | Weinberg et al. ............ 250/288 |
| 5,999,262 A * | | 12/1999 | Dobschal et al. ............ 356/504 |
| 6,043,506 A * | | 3/2000 | Heffelfinger et al. ........ 250/584 |
| 6,097,034 A * | | 8/2000 | Weckstrom et al. ...... 250/495.1 |
| 6,426,226 B1 * | | 7/2002 | Senkan ........................ 436/37 |
| 6,538,251 B1 * | | 3/2003 | Weckstrom et al. .......... 250/343 |
| 6,576,906 B1 * | | 6/2003 | Archibald et al. ......... 250/341.4 |
| 6,849,460 B2 * | | 2/2005 | McFarland et al. .......... 436/171 |
| 2002/0017617 A1 * | | 2/2002 | Schuth et al. ............. 250/492.1 |
| 2002/0030163 A1 * | | 3/2002 | Zhang ......................... 250/330 |
| 2003/0044967 A1 * | | 3/2003 | Heffelfinger et al. ..... 435/287.2 |
| 2003/0071996 A1 * | | 4/2003 | Wang et al. .................. 356/369 |
| 2003/0101006 A1 * | | 5/2003 | Mansky et al. ................. 702/30 |
| 2004/0071860 A1 * | | 4/2004 | Newsam et al. .............. 427/2.1 |

FOREIGN PATENT DOCUMENTS

| | | |
|---|---|---|
| DE | 196 15 366 | 10/1997 |
| DE | 100 16 358 | 10/2000 |
| DE | 199 18 956 | 11/2000 |
| DE | 100 14 816 | 8/2001 |
| DE | 100 12 847 | 9/2001 |
| DE | 101 02 218 | 8/2002 |
| EP | 0 744 601 | 11/1996 |
| EP | 0 953 838 | 11/1999 |
| JP | 60-039533 | 3/1985 |

* cited by examiner

*Primary Examiner*—David P Porta
*Assistant Examiner*—Faye Boosalis
(74) *Attorney, Agent, or Firm*—Kenyon & Kenyon LLP

(57) ABSTRACT

A device for analyzing a materials library includes at least one radiation source for electromagnetic radiation, which is positioned in front of the materials library, and at least two flat detectors operating in parallel, which are operable using high-sensitivity resolution and of which one is sensitive to electromagnetic radiation of a first wavelength range and the other is sensitive to electromagnetic radiation of a second wavelength range. Moreover, a method for analyzing a materials library in which the materials library is simultaneously tested using at least two methods in which electromagnetic radiation of different wavelength ranges is used. The beam is split behind the materials library as a function of wavelength and is deflected in the direction of at least two flat sensors operating using high-sensitivity resolution.

6 Claims, 1 Drawing Sheet

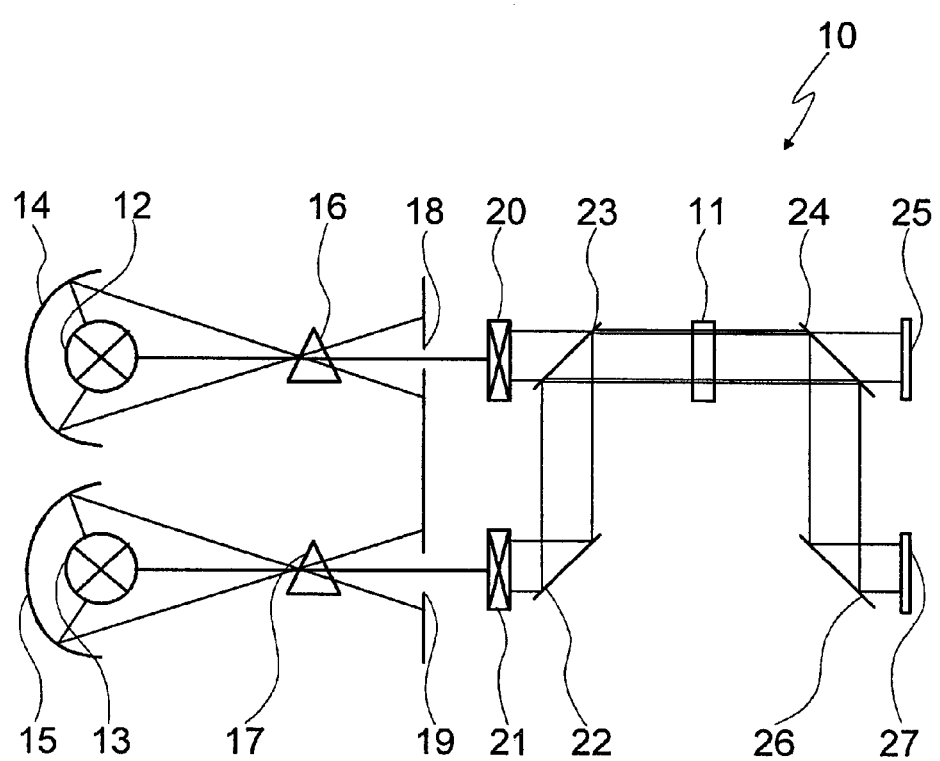

DEVICE AND METHOD FOR ANALYZING A MATERIALS LIBRARY

BACKGROUND INFORMATION

In order to be able to develop materials that are used, for example, for sensors or also for catalysts, it is presently customary to use high throughput methods in which a materials library is created, the elements of which are tested with respect to properties of significance to the particular application. The elements or materials of the materials library are primarily tested for the desired target property. Thus in the case of resistive sensors, the material having the best resistance properties is determined, in the case of optical sensors, the optical absorption characteristics and in the case of catalysts, substance conversion is analyzed.

For example, for the development of an optical sensor that changes color under the influence of a gas, it is known from common practice to irradiate a materials library using visible light and to analyze it by spectroscopy using a corresponding detector, which is sensitive to this wavelength range.

Moreover, for the development of a sensor, it is known to apply infrared radiation to a materials library and to measure the resulting infrared spectra for the individual elements using a flat infrared detector. A spectroscopic test of this type makes it possible to analyze the chemical reactions occurring in the individual elements of the materials library. 10

The spectroscopic tests make it possible to select the element from the materials library in question that has the best properties for the particular application. In order to optimize the selection of materials, various spectroscopic methods have been used in succession in the past. At times, this may be very time-intensive.

SUMMARY OF THE INVENTION

The device of the present invention for analyzing a materials library has the advantage that the elements of the materials library may be tested with respect to their properties simultaneously with a plurality of, in particular, spectroscopic methods. This results in greatly speeding up the determination of a material suitable for a specific application. Through the use of the materials library, the device of the present invention is designed for the implementation of a high throughput method in which the suitable material is to be determined according to combinatory chemical methods.

The elements or materials of the materials library may be solids, liquids or even gases, which may be analyzed using frequency-dependent methods.

For example, it is possible to analyze materials for an optical sensor using the device of the present invention simultaneously with respect to at least two properties. It is thus possible to use the device of the present invention to characterize the absorption characteristics of the elements, i.e., the target variable, using absorption spectra and also to analyze chemical reactions occurring in the elements of the materials library using infrared spectroscopy.

The clarification of the particular reaction mechanisms simultaneously with the determination of a change in absorption representing a sensor signal makes a targeted further development of materials possible.

The device of the present invention may be used in conjunction with a plurality of spectroscopic methods. In principle, the device may be designed in such a way that it is possible to determine emission, excitation, diffusion and/or reflection spectra of the elements of the materials library.

It is also conceivable, with the device of the present invention, to provide spectroscopy methods based on the interaction of particles with matter, such as is the case, for example, with electron spectroscopy for chemical analyses (ESCA).

For example, the device is designed in such a way that it is possible to perform infrared spectroscopy, UV spectroscopy, VIS spectroscopy, Raman spectroscopy, microwave spectroscopy, fluorescence spectroscopy, phosphorescence spectroscopy and/or Auger spectroscopy simultaneously.

In the test of materials libraries, whose elements are catalysts, the catalytic properties, i.e., the properties of the particular elements that speed up a chemical reaction, may be inferred from the heat tone of the elements. The heat tone is determined using a corresponding, flat IR detector, which represents the first flat detector. In this case, the device of the present invention has only one radiation source, for example, a radiation source emitting a UV radiation, by means of which the materials library is irradiated so that it is possible to implement a second spectroscopy method using the second flat detector.

In a preferred embodiment, however, the device of the present invention has two radiation sources, one of which emits a radiation of a first wavelength range and the second one emits a radiation of a second wavelength range. Thus the first wavelength range may be, for example, in the range of visible light and the second in the infrared range.

A device designed in this manner may be used in particular to analyze a materials library whose elements are intended for use with optical sensors.

In order to be able to assign the individual wavelength ranges, which are intended to be used for a spectral analysis, unambiguously to one of the flat detectors, the device of the present invention preferably includes at least one wavelength-sensitive mirror which is positioned behind the materials library and in front of the flat detectors. A wavelength-sensitive or semi-transparent mirror of this type reflects the one wavelength range and is transparent for the other wavelength range.

It is advantageous in particular to position at least one wavelength-sensitive mirror both in front of and behind the materials library so that radiation of different wavelengths emitted by at least two radiation sources is combined into one bundle of rays in front of the materials library and may be split again as a function of wavelength or frequency behind the materials library. It is thus possible in a convenient manner to transmit a radiation beam onto or through the materials library using radiation from a plurality of frequency ranges in parallel and simultaneously. The wavelength-sensitive mirrors are formed, for example, from a heat reflecting filter that reflects infrared radiation and transmits visible light.

In order to filter out radiation of a specific wavelength, a monochromator may be positioned downstream from the radiation source or radiation sources.

To produce a bundle of rays from the radiation emitted by the particular radiation source, an optical system may also be assigned to each radiation source.

In order to be able to analyze, for example, materials for a gas sensor, the device of the present invention may also include a gas source to apply the gas in question to the materials library.

Moreover, an object of the present invention includes a method for analyzing a materials library. In the method, the elements of the materials library are simultaneously tested using two methods, which use the electromagnetic radiation of different wavelength ranges.

In the method, electromagnetic radiation, which is assigned to at least two different wavelength ranges, is preferably applied to the materials library. The resulting spectra are advantageously determined using two detectors sensitive to the wavelength ranges in question, the radiation behind the materials library being split according to wavelength sensitivity or frequency selectivity and deflected to the detector in question.

BRIEF DESCRIPTION OF THE DRAWING

The FIGURE shows a device for analyzing a materials library using two spectroscopic methods.

DETAILED DESCRIPTION

The FIGURE shows a device 10 for analyzing a materials library 11, which in the present case is made up of a plurality of elements or substances, each of which being usable as an optical sensor and are here situated on a combinatory substrate.

Device 10 includes two radiation sources 12 and 13, a reflection mirror 14 and 15, respectively being assigned to each of them. Radiation source 12 emits infrared radiation and radiation source 13 emits visible light.

Positioned downstream from radiation sources 12 and 13 is one monochromator 16 and 17, respectively, which selects radiation of a specific wavelength from the frequency spectrum emitted by radiation sources 12 and 13. A gap 18 and 19, respectively, is located behind monochromatic illuminators 16 and 17, the radiation from the particular radiation source being transmitted through the gap and then striking an optical system 20 and 21, respectively. Each of optical systems 20 and 21 includes a plurality of lenses, which generate a bundle of rays from the incident beam.

In order to deflect both the bundle of rays generated by optical system 20 as well as the bundle of rays generated by optical system 21 to materials library 11, device 10 includes a first deflection mirror 22 which deflects the bundle of rays generated by optical system 21 by 90°, specifically in the direction of a first wavelength-sensitive diversion mirror 23, on which the radiation coming from diversion mirror 22 is reflected in the direction of materials library 11. Diversion mirror 23 is situated in the beam path of the infrared radiation bundled by optical system 20 and transmits this radiation in the direction of materials library 11. Diversion mirror 23 is made up of a silicon wafer so that it transmits infrared radiation and reflects visible light.

Behind materials library 11, the bundle of rays strikes a second wavelength-sensitive diversion mirror 24, which in turn is made up of a silicon wafer and thus also reflects visible light and transmits infrared radiation.

Infrared radiation coming from materials library 11 thus passes through second diversion mirror 24 and strikes flat detector 25, an IR focal plane detector, which is positioned behind diversion mirror 24. Flat detector 25 operates using high-sensitivity resolution so that an array of flat detector 25 is assignable to each element of materials library 11.

Visible light coming from materials library 11 is reflected on second diversion mirror 24 in the direction of a second deflection mirror 26, which in turn reflects this light in the direction of a second flat detector 27, which is sensitive in the wavelength range of visible light and is designed as a VIS focal plane detector. Detector 27 consequently also operates using high-sensitivity resolution so that an array of flat detector 27 is assignable to each element of materials library 11.

The measuring system implemented using device 10 makes it possible to investigate materials library 11 simultaneously according to an IR spectroscopic method as well as a VIS spectroscopic method.

What is claimed is:

1. A device for analyzing a materials library comprising:
at least two radiation sources for emitting electromagnetic radiation, situated in front of the materials library, a first of the at least two radiation sources emitting electromagnetic radiation in one of (a) an infrared wavelength range and (b) a Raman wavelength range and a second of the at least two radiation sources emitting electromagnetic radiation in one of (a) a UV wavelength range and (b) VIS wavelength range; and
at least two flat detectors operating in parallel and operable using high-sensitivity resolution, a first of the at least two flat detectors being sensitive to electromagnetic radiation in one of (a) the infrared wavelength range and (b) the Raman wavelength range and a second of the at least two flat detectors being sensitive to electromagnetic radiation in one of (a) the UV wavelength range and (b) the VIS wavelength ranged,
wherein the device is capable of simultaneously analyzing a plurality of elements in the materials library.

2. The device according to claim 1, further comprising at least one wavelength-sensitive mirror situated behind the materials library and in front of the flat detectors.

3. The device according to claim 1, further comprising at least one optical system for bundling the radiation emitted by at least one of the at least two radiation sources, the at least one optical system being assigned to the at least one of the at least two radiation sources.

4. The device according to claim 1, further comprising at least one monochromator assigned to at least one of the at least two radiation sources.

5. The device according to claim 1, further comprising a gas source for applying a gas to the materials library.

6. A method for analyzing a materials library, the method comprising:
simultaneously testing a plurality of elements in the materials library using at least two methods in which electromagnetic radiation of different wavelength ranges is used, wherein at least two radiation sources for emitting electromagnetic radiation are used, a first of the at least two radiation sources emitting electromagnetic radiation in one of (a) an infrared wavelength range and (b) a Raman wavelength range and a second of the at least two radiation sources emitting electromagnetic radiation in one of (a) a UV wavelength range and (b) VIS wavelength range;
performing a wavelength-dependent beam splitting behind the materials library; and
deflecting the radiation in a direction of at least two flat sensors operating using high-sensitivity resolution, the at least two flat sensors being sensitive to different wavelength ranges;
wherein a first wavelength range is in one of (a) the infrared wavelength range and (b) the Raman wavelength range and a second wavelength range is in one of (a) the UV wavelength range and (b) the VIS wavelength range.

* * * * *